US00PP30160P2

(12) United States Plant Patent
Tsukahara

(10) Patent No.: US PP30,160 P2
(45) Date of Patent: Jan. 29, 2019

(54) COLEUS PLANT NAMED 'SAKCOL021'

(50) Latin Name: ***Solenostemon* sp.**
Varietal Denomination: SAKCOL021

(71) Applicant: Sakata Seed Corporation, Tsuzuki-Ku, Yokohama (JP)

(72) Inventor: Jun Tsukahara, Kakegawa Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/732,580

(22) Filed: Nov. 29, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Keith O. Robinson
(74) *Attorney, Agent, or Firm* — Bethany R. Roahrig; Barbara Campbell; Cochran Freund & Young LLC

(57) ABSTRACT

A coleus plant particularly distinguished by long leaves having shades of pink and dark burgundy inner leaf color and green margins, is disclosed.

1 Drawing Sheet

Genus and species: *Solenostemon* sp.
Variety denomination: 'SAKCOL021'.

BACKGROUND OF THE NEW PLANT

The present invention comprises a new and distinct variety of coleus, botanically known as *Solenostemon* sp., and hereinafter referred to by the variety name 'SAKCOL021'.

'SAKCOL021' originated from the open pollination of 8 unpatented proprietary lines crossed pollinated in October 2014 in Kakegawa, Japan. The breeder put breeding materials '14P-202', '14P-203', '14P-205', '14P-210', '14P-211', '14P-212', '14F-19',and '14F-20-2' in a cage. Bees then crossed them at random. The breeder harvested 1,200 seeds from '14P-211'. These seeds were composed of hybrid seeds and self-pollinated seeds.

The seeds obtained from the '14P-211' plant were sown and a single plant selection designated 'L2015-C0202' (not patented) was selected for its multi-colored leaf pattern with shades of pink and dark burgundy inner leaf color and green margins with mounding plant habit with long leaves. The breeder confirmed that 'L2015-CO202' was fixed and stable. 'L2015-CO202' was subsequently named 'SAKCOL021'.

The new plant was first asexually propagated from October 2015 to April 2016 in Japan and has been asexually reproduced by vegetative cuttings for almost three years in Japan. The present invention has been found to retain its distinctive characteristics through successive asexual propagations by vegetative cuttings.

'SAKCOL021' has not been made publicly available or sold more than one year prior to the filing date of this application.

SUMMARY OF THE NEW PLANT

The following are the most outstanding and distinguishing characteristics of the new variety when grown under normal horticultural practices in Salinas, Calif.

1. Small leaves; and
2. Pink and rose inner leaf color and green margins.

DESCRIPTION OF THE PHOTOGRAPHS

This new coleus plant is illustrated by the accompanying photograph which shows the overall plant habit, and foliage of a plant aged 3 months old. The colors are as true as can be reasonably obtained by conventional photographic procedures.

DESCRIPTION OF THE NEW VARIETY

The following detailed descriptions set forth the distinctive characteristics of 'SAKCOL021'. The data which defines these characteristics were collected from plants grown three months from transplant into 4-inch pots from rooted cuttings in Salinas, Calif., under greenhouse conditions. Color references are to The Royal Horticultural Society Colour Chart, $4^{th}$ edition. Anatomic labels are from *The Cambridge Illustrated Glossary of Botanical Terms*, by M. Hickey and C. King, Cambridge University Press.

Classification:
- *Family*.—Lamiaceae.
- *Botanical name*.—*Solenostemon* sp.
- *Common name*.—Coleus.
- *Denomination*.—'SAKCOL021'.

Plant:
- *Type*.—Annual.
- *Habit*.—Very dense.
- *Form*.—Compact and very dense, 5 main branches.
- *Height*.—19.0 cm.
- *Spread*.—29.0 cm.
- *Propagation type*.—Vegetative cuttings.

Environmental conditions for plant growth: The terminal 1.0 to 1.5 inches of an actively growing stem was excised. The vegetative cuttings were propagated for five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24 degrees C.

Lateral branches:

*Length.*—6.5 cm to 15.0 cm.

*Diameter.*—0.6 cm to 1.0 cm.

*Internode length.*—0.8 cm to 1.0 cm.

*Strength.*—Branches separate easily.

*Aspect.*—Large.

*Shape in cross-section.*—Square.

*Texture.*—Dull, very slight pubescent.

*Pubescence color.*—RHS N155A (White).

*Stem/branch color.*—Closest to RHS 144B (Yellow-Green).

*Flowering branch.*—Absent.

Leaves:

*Arrangement.*—Opposite, having small mature foliage close to the stalk and much larger mature leaves on exterior.

*Small mature foliage.*—Length: 5.5 cm. Width: 2.3 cm.

*Large mature foliage.*—Length: 10.2 cm. Width: 4.4 cm.

*Broadest part of the leaf blade.*—Middle.

*Shape.*—Pinnatipartite.

*Apex.*—Caudate.

*Base.*—Acuminate.

*Margin.*—Sinuate.

*Texture, upper surface.*—Dull, very slight pubescence.

*Texture, lower surface.*—Glabrous with pronounced venation.

*Venation pattern.*—Reticulate.

*Vein color, upper surface.*—RHS 59A (Red-Purple).

*Vein color, lower surface.*—Closest to RHS 148B (Yellow-Green) with RHS 59A (Red-Purple) towards petiole.

*Small mature foliage.*—Petiole length: 2.1 cm. Petiole diameter: 1.5 mm.

*Large mature foliage.*—Petiole length: 6.1 cm to 9.3 cm. Petiole diameter: 2.5 mm.

*Petiole color, small and large foliage.*—Closest to RHS 144B (Yellow-Green) with very slight RHS 59A.

*Petiole texture.*—Very slight pubescent.

*Variegation.*—Present.

*Leaf color.*—Multicolored, mostly dark burgundy with shades of pink at the center and green at margin. Upper surface: Closest to but darker than RHS 200A (Brown) with RHS 59B (Red-Purple) at center and RHS 146A (Yellow-Green) at margin. Lower surface: Closest to RHS 148B (Yellow-Green) with blotches of RHS N77A (Purple) increasing around venation.

Reproductive organs: No flowers observed.

Temperature tolerance: 2 degrees C. to 35 degrees C.

Disease or insect resistance: No disease or insect resistance observed.

COMPARISON WITH PARENTAL LINES AND KNOWN VARIETY

'SAKCOL021' is a new and distinct cultivar of coleus owning to its unique multicolored leaf pattern and mounding plant habit and small leaves. It is distinguished from its parents as described in Table 1 below.

TABLE 1

Comparison with Parental Lines

| Parental lines | Leaf color | Leaf size | Leaf shape | Leaf margin | Plant habit |
|---|---|---|---|---|---|
| '14P-202' | Brown | Extremely small | Orbicular, | Crenate | Creeping |
| '14P-203' | Rose and green | Extremely small | Orbicular | Crenate | Creeping |
| '14P-205' | Brown | Extremely small | Orbicular | Crenate | Creeping |
| '14P-210' | Rose and brown | Small | Ellipse | Serrate | Mounding |
| '14P-211' | Rose and green | Small | Ellipse | Serrate | Mounding |
| '14P-212 | Rose, brown and green | Large | Ovate | Crenate | Erect |
| '14F-19' | Dark brown and green | Medium | Ovate | Crenate | Erect |
| '14F-20-2' | Rose, brown and green | Extremely large | Orbicular | Crenate | Erect |
| **Comparison** | **Leaf color** | **Leaf size** | **Leaf shape** | **Leaf margin** | **Plant habit** |
| 'SAKCOL021' | Closest to but darker than RHS 200A (Brown) with RHS 59B (Red-Purple) at center and RHS 146A (Yellow-Green) at margin | Small Length: 10.2 cm Width: 4.4 cm | Pinnatipartite | Sinuate | Mounding |

'SAKCOL021' is most similar to the commercial variety PARTY TIME 'Sangria' (not patented). However, there are differences as listed in Table 2 below.

TABLE 2

Comparison with Similar Variety

| Characteristic | 'SAKCOL021' | PARTY TIME 'Sangria' |
|---|---|---|
| Leaf color, upper surface | Closest to but darker than RHS 200A (Brown) with RHS 59B (Red-Purple) at center and RHS 146A (Yellow-Green) at margin | N77A (Purple) with Mid-vein: RHS N77A (Purple), Center: closest to RHS 183C (Greyed-Purple), with RHS 143A (Yellow-Green) at edge. |
| Leaf color, lower surface | Closest to RHS 148B (Yellow-Green) with blotches of RHS N77A (Purple) increasing around venation | 147B (Yellow-Green), with blotches of RHS 59A (Red-Purple) at center Mid-vein & Netting: RHS 145C (Yellow-Green) |
| Plant growth habit | Compact, Mounding | Compact, Erect |

I claim:

1. A new and distinct variety of coleus plant named 'SAKCOL021' as illustrated and described herein.

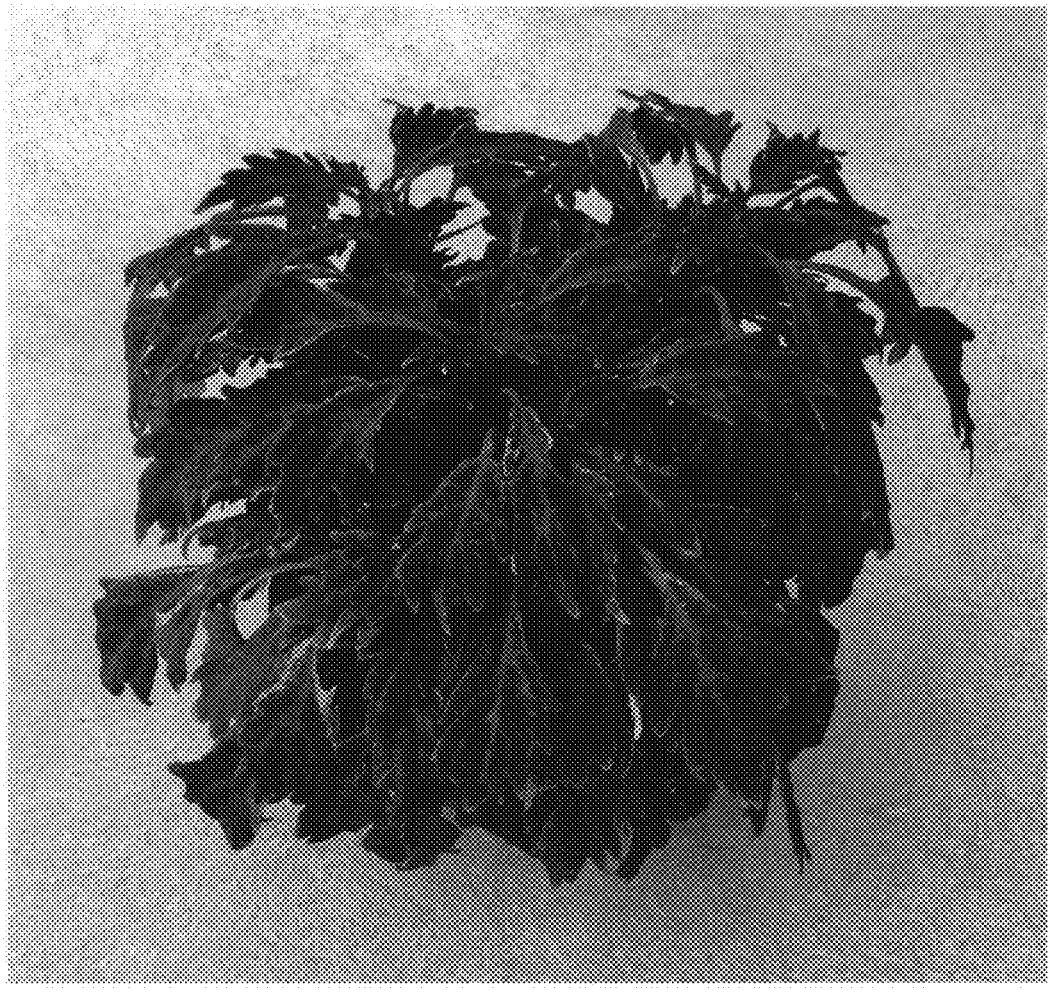

* * * * *